(12) United States Patent
Ling et al.

(10) Patent No.: US 6,214,053 B1
(45) Date of Patent: *Apr. 10, 2001

(54) PROSTHESIS WITH CENTRALIZER AND CENTRALIZER FOR USE THEREWITH

(75) Inventors: Robin Sydney Mackwood Ling, Dartmouth; Graham Allan Gie, Yeoford; Andrew John Timperley, St. Leonards, all of (GB); John Andrew Storer, Bayeux (FR)

(73) Assignee: Benoist Girard SAS (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 3 days.

(21) Appl. No.: 09/323,619

(22) Filed: Jun. 1, 1999

(30) Foreign Application Priority Data

Jun. 4, 1998 (GB) .................................................. 9812068

(51) Int. Cl.[7] ......................................................... A61F 2/36
(52) U.S. Cl. ..................................... 623/23.11; 623/23.48; 623/16.11; 623/18.11; 623/22.4
(58) Field of Search ................................... 623/19, 18, 16, 623/22, 23, 18.11, 16.11, 22.11, 22.43, 22.4, 22.46, 23.11, 23.46, 23.47, 23.48, 23.52, 23.44; 606/62, 67, 95, 94

(56) References Cited

U.S. PATENT DOCUMENTS

| | | | |
|---|---|---|---|
| 4,064,567 | 12/1977 | Burnstein et al. | 623/23.46 |
| 4,827,919 | 5/1989 | Barbarito et al. | 128/92 |
| 4,846,839 * | 7/1989 | Noiles | 623/18.11 |
| 4,881,536 * | 11/1989 | Noble et al. | 623/22 |
| 5,035,717 | 7/1991 | Brooks | 623/18 |
| 5,080,680 | 1/1992 | Mikhail et al. | 623/23 |
| 5,092,892 | 3/1992 | Ashby | 623/16 |
| 5,116,380 | 5/1992 | Hewka et al. | 623/23 |
| 5,163,963 | 11/1992 | Hewka et al. | 623/23 |
| 5,171,288 | 12/1992 | Mikhail et al. | 623/23 |
| 5,197,990 | 3/1993 | Lawes et al. | 623/23 |
| 5,290,311 | 3/1994 | Baumann | 623/23 |
| 5,314,489 | 5/1994 | Hoffman et al. | 623/22 |
| 5,340,362 | 8/1994 | Carbone | 623/23 |
| 5,443,523 | 8/1995 | Mikhail | 623/23 |
| 5,470,336 | 11/1995 | Ling et al. | 606/105 |
| 5,507,832 | 4/1996 | Michielli et al. | 623/23 |
| 5,549,705 | 8/1996 | Michielli et al. | 623/23 |
| 5,571,204 | 11/1996 | Nies | 623/23 |
| 5,658,351 | 8/1997 | Dudasik et al. | 623/23 |
| 5,665,121 * | 9/1997 | Gie et al. | 623/16 |
| 5,755,720 * | 5/1998 | Mikhail | 623/22 |
| 5,766,262 | 6/1998 | Milhail | 623/23 |
| 5,788,704 * | 8/1998 | Temperley | 606/95 |
| 5,885,295 * | 3/1999 | McDaniel et al. | 606/95 |

\* cited by examiner

*Primary Examiner*—Pedro Philogene
(74) *Attorney, Agent, or Firm*—Lerner, David, Littenberg, Krumholz & Mentlik, LLP

(57) ABSTRACT

A prosthesis provided with a device for guiding its stem in a bone cavity and in which it is to be attached by cement. The sleeve guiding device comprises a sleeve having an opening to receive the stem and locate the sleeve on the stem at a position at or towards its proximal end. The is dimensioned and adapted to locate the stem in a predetermined position within the cross-sectional area of the bore of the bone cavity.

33 Claims, 4 Drawing Sheets

PROSTHESIS WITH CENTRALIZER AND CENTRALIZER FOR USE THEREWITH

BACKGROUND OF THE INVENTION

1. Field of the Invention

This invention relates to a prosthesis with a centraliser and centraliser for use therewith.

2. Description of the Prior Art

It is known to provide the stem of at femoral prosthesis with a centraliser at or towards the distal tip of its stem. There are however difficulties in guiding the proximal end of the stem in the bone cavity to which it is to be attached by cement and the present invention is intended to overcome the difficulties involved.

SUMMARY OF THE INVENTION

According to the present invention a prosthesis is provided with a device for guiding its stem in a bone cavity and which is to be attached by cement, said guiding device comprising a sleeve having an opening to receive said stem and locate it on said stem at a position at or towards its proximal end and which is dimensioned and adapted to locate the stem in a predetermined position within the cross-sectional area of the bore of the bone cavity.

In one embodiment according to the invention the sleeve extends over only a part of the length of the stem spaced away from the distal end thereof.

In another construction the sleeve can be arranged to extend over the whole length of the stem.

The outer shape of the sleeve can take various forms and in a convenient construction the sleeve has a wall thickness which is increased towards its proximal end to provide an outwardly projecting balcony.

The outer shape of the sleeve can be formed with one or more concave surfaces the proximal end or ends of which form said balcony.

Alternatively the outer shape of the sleeve can be formed with one or more substantially flat surfaces the proximal ends of which form said balcony.

In one preferred construction the sleeve has an outer shape which is conical or frusto-conical and thus it has only one outer surface which provides the concave surface referred to above.

In another construction the sleeve can have an outer shape which includes three or more flat surfaces which are curved inwardly from its proximal end. With such a construction the sleeve can have a cross-sectional outer shape which is triangular, square or rectangular.

When a sleeve extends over the whole length of the stem the distal end of the sleeve can enclose the stem and be provided with a cup into which the distal end of the stem can subsequently sink and said cup can be arranged to extend up to half the length of the stem from its distal end.

If desired the sleeve can be provided with means for distally centralising the stem in the bone canal.

In another construction the sleeve can be arranged to cover the stem from a point adjacent the proximal end of the bone when the stem is inserted to a point spaced away from the distal tip.

The sleeve can be preformed and subsequently fitted to the stem.

The sleeve can be made from any convenient material, for example polymethylmethacrylate (PMMA).

The invention also includes a device for guiding the proximal end of the stem of a prosthesis in a bone cavity and which is to be attached by cement, and comprising a sleeve having an opening to receive said stem and adapted to locate on said stem at a position at or towards its proximal end, and which is dimensioned to engage the wall of the bone cavity at or towards the proximal end thereof to guide the proximal end of the stem in place therein.

This device can have all the features referred to above.

BRIEF DESCRIPTION OF THE DRAWINGS

The invention can be performed in many ways and some embodiments will now be described by way of example anid with reference to the accompanying drawings in which.

DESCRIPTION OF THE PREFERRED EMBODIMENTS

Figure 2:
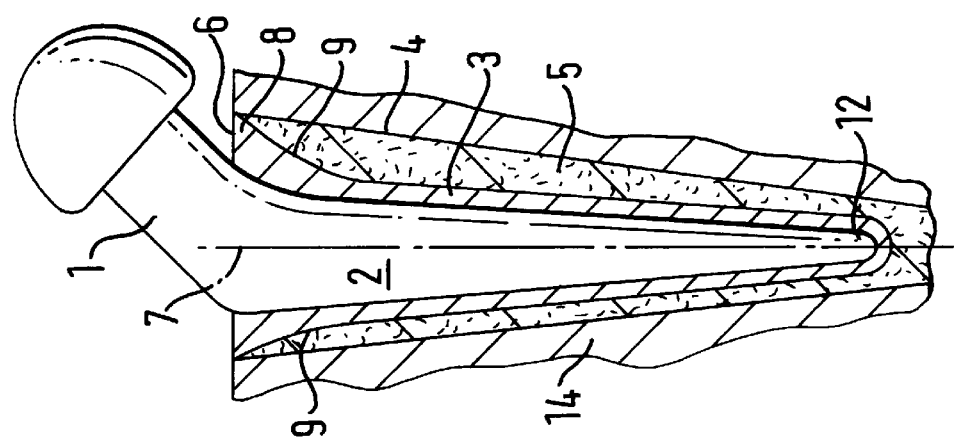
FIG. 2 is a cross-sectional side elevation of a femoral prosthesis provided with a device according to the invention.
Figure 1:
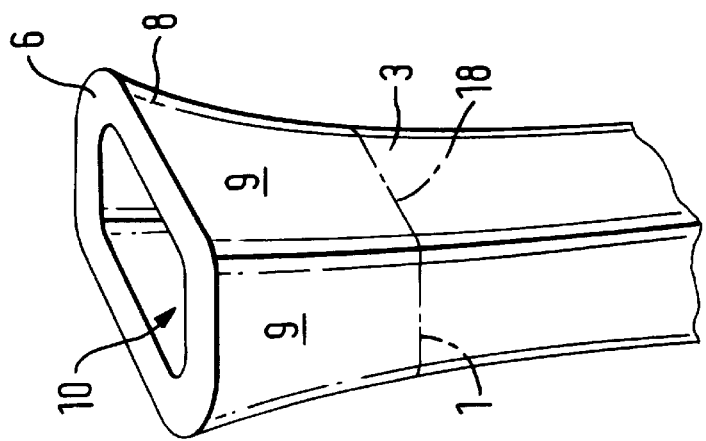
FIG. 1 is an isometric view of part of a device for guiding the proximal end of the stem of a prosthesis according to the invention.

As shown in FIGS. 1 and 2 a prosthesis 1 according to the invention is provided with a stem 2 which is enclosed in a proximal guiding device in the form of a sleeve 3 and which is shown inserted in a bone cavity 4 filled with cement 5. As will be seen from FIG. 2 the wall thickness of the sleeve 3 is increased towards its proximal end 6 which is adjacent the proximal end 7 of the stem 2 to provide an outwardly projecting balcony 8. Concave surfaces 9 are provided, the proximal ends of which form the balcony 8.

In the construction shown in FIGS. 1 and 2 the sleeve is used on a stem having flat sides and thus the proximal end opening 10 is substantially rectangular as will be seen from FIG. 1. The sleeve has an outer shape which includes four flat concave surfaces 9 and which are curved inwardly from the proximal end 6.

The sleeve covers the stem from its distal tip 12 to a point adjacent the proximal cut end 13 of the bone 14 when the stem is inserted.

The distal end of the sleeve need not necessarily cover the distal end of the stem 2.

It will be seen that the proximal end of the balcony 8 is shaped to engage the walls 4 of the bone cavity so that when the cavity has been filled with cement 5 and the prosthesis is inserted into it the concave surfaces 9 act to pressurise the cement as the final part of the entry is made. As the balcony engages the side walls 4 of the cavity it acts to guide the prosthesis and at the same time seal the cavity and prevent escape of cement.

Figure 3:
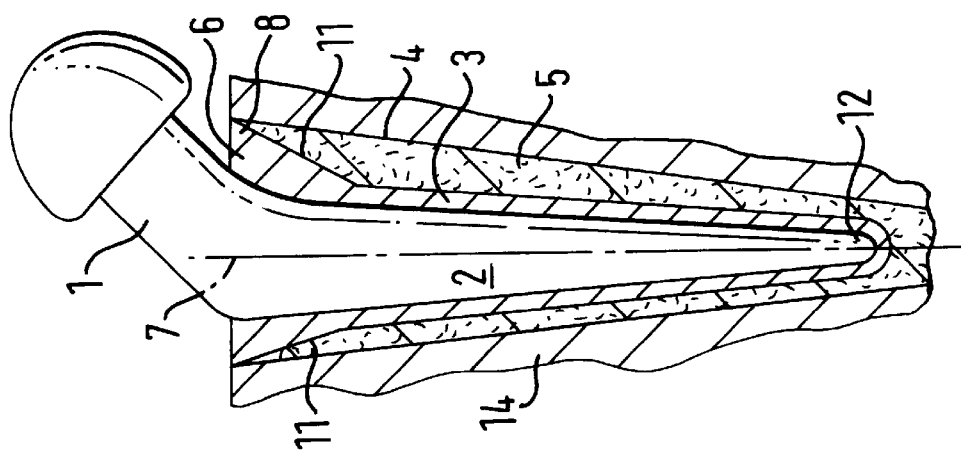
FIGS. 3 and 4 are views similar to FIG. 2 showing different forms of device.

Another construction according to the invention is shown in FIG. 3 in which the same reference numerals are used to indicate the same parts as those shown in FIGS. 1 and 2. In this construction the concave surfaces 4 are replaced by substantially flat surfaces 11 the proximal ends of which form the balcony 8. The effect is similar to that described with regard to FIGS. 1 and 2.

Figure 4:
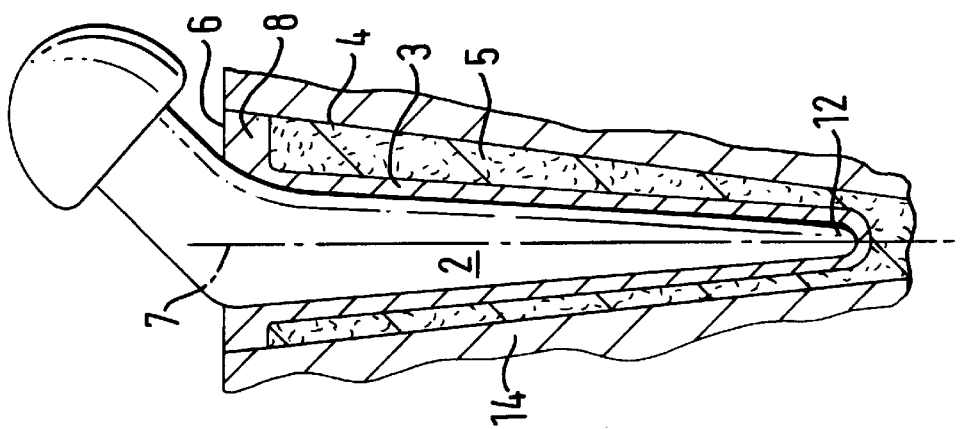

FIG. 4 shows another alternative construction in which the same reference numerals as those used in FIGS. 1 and 2 are again employed for similar parts. In this construction the surface of the balcony 8 is cut back to provide what is, in effect, a flange which once again operates in the manner described.

The sleeve could be provided with a distal centraliser, for example of the kind shown in U.S Pat. No. 5,197,990 or a separate centraliser could be employed which is applied externally of the sleeve.

Figure 5:
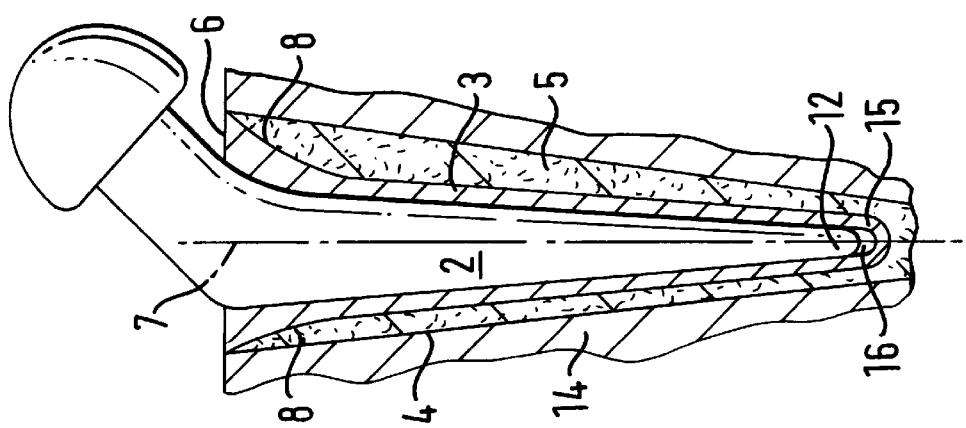
FIG. 5 is a view similar to FIG. 2 showing different forms of sleeve.

FIG. 5 shows another construction similar to that shown in FIGS. 1 and 2 and the same reference numerals are used to indicate similar parts. In this construction however the distal end 15 of the sleeve is extended to provide a void 16 into which the stem 2 can subsequently sink after insertion. The balcony shape could be as shown in any of FIGS. 1 to 4.

The sleeve can be formed on the stem of the prosthesis or it can be preformed as a separate article and suitably dimensioned and adapted for subsequent fitting to the stem of the prosthesis.

The sleeve can be made from any suitable material but is preferably made from a material similar to bone cement, for example polymethylmethacrylate (PMMA) so that it has a good adherence with the bone cement used in the bone cavity.

In the arrangements described above the cross-section of the sleeve is substantially rectangular but surfaces beneath the balcony could be triangular, square or any other convenient shape which is suitable for the particular cross-sectional shape of the prosthesis stem.

Again, if the prosthesis stem is substantially circular in cross-section then flat or concave surfaces can again be used or the outer shape of the sleeve can be substantially conical or frusto-conical beneath the balcony 8 thus providing a single surface at that portion.

Figure 6:
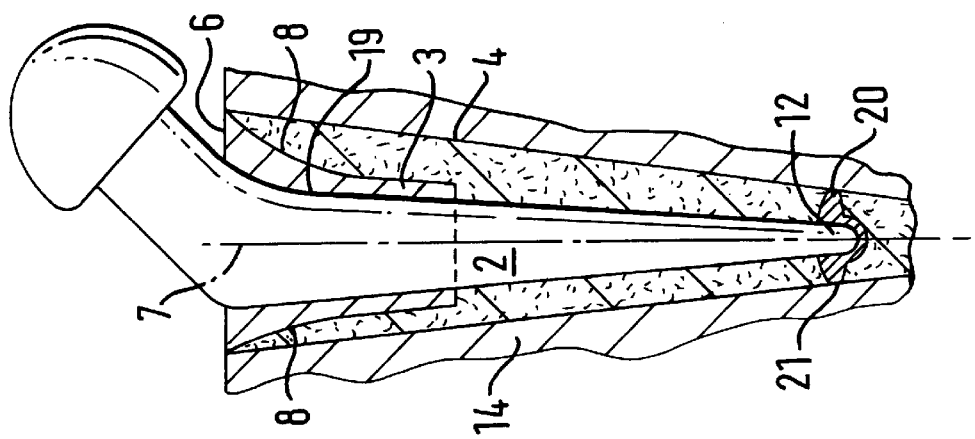
FIG. 6 is a cross-sectional side elevation showing a shortened form of device in position on a femoral prosthesis.

FIG. 1 also shows an alternative form of sleeve which can be used as shown in FIG. 6. Once again similar reference numerals are used to indicate similar parts. In this construction the sleeve 3 is a similar shape to that shown in the other constructions but the sleeve only extends downwardly for the distance shown above the broken lines 18 in FIG. 1. As will be seen from FIG. 6 the sleeve only extends for about one third of the length of the stem and is indicated by reference numeral 19. This sleeve acts in a similar way to that described with regard to the other Figures and again acts as a proximal guide for the stem 2. An additional distal centraliser 20 is shown which is located on the distal end 12 of the stem 2 and is provided with radially extending location wings or fins 21. The centraliser can be made from any convenient material and is preferably resilient so that it can locate in the bone cavity appropriately.

As described with regard to FIGS. 2 and 3 the sleeve 19 can be made as a separate article and be subsequently fitted to the stem.

Figure 7:
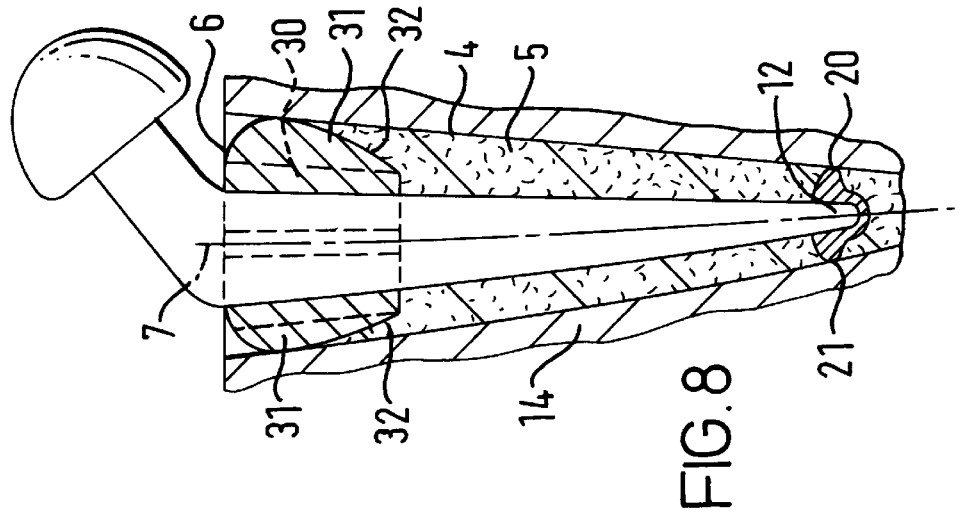
FIG. 7 is a cross-sectional side elevation of another construction.

In the arrangements described above the outer wall of the proximal guide provided by the sleeve is cut away but another construction is shown in FIG. 7. This is a construction similar to that shown in FIG. 6 and the same reference numerals are used to indicate similar parts but in this construction substantially the whole of the outer surface 25 of the sleeve 26 engages substantially the whole of the proximal end portion of the wall of the bone cavity 4.

Figure 8:
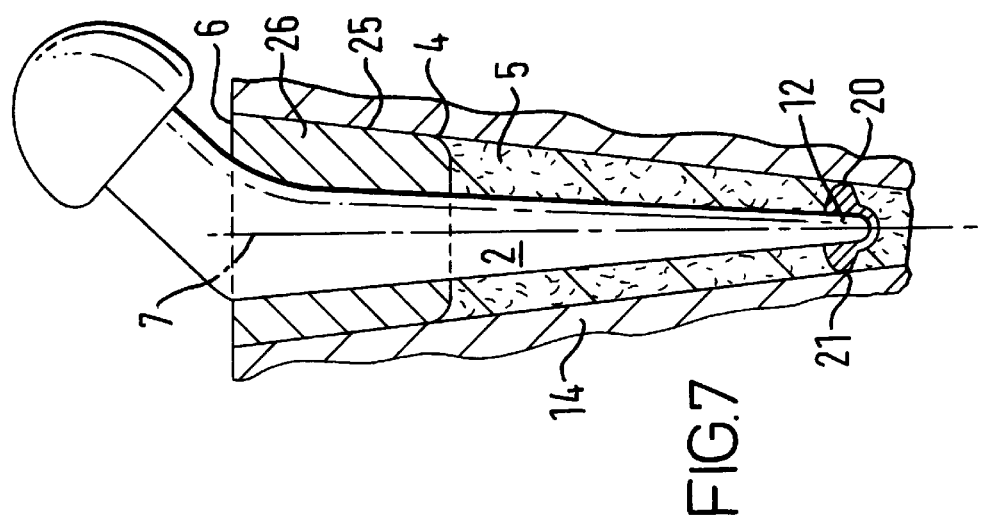
FIG. 8 shows another alternative construction according to the invention.

FIG. 8 shows a cross-sectional side elevation of another guide construction according to the invention and the same reference numerals are used to indicate similar parts to those shown in FIGS. 6 and 7.

In this construction the guide is formed as a central sleeve 30 which is adapted to fit onto the proximal end of the stem 2. Projecting outwardly from the sleeve 30 are four wings 31 the outer surfaces 32 of which are of curved shape and are adapted to engage the inner wall of the bone cavity 4.

These wings can be resilient and the device can again be made from a bone cement or any other suitable material, even metal.

Other forms of wing can be used, for example they can be in the form of outwardly biased springs projecting upwardly from the distal end of the sleeve 30. The outer ends of these springs which would provide the outer surfaces of the device would again contact the inner walls of the bone cavity 4.

The wings could be rigid to guide the stem into a prepared cavity of known dimensions.

Figure 9:
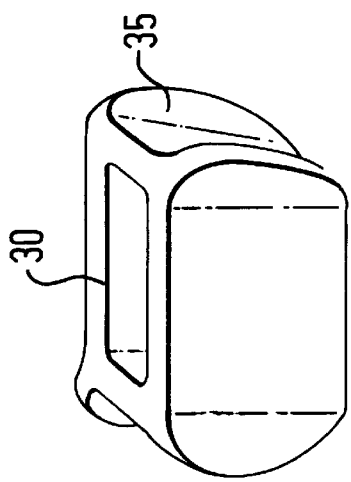
FIG. 9 is an isometric view of another sleeve construction.

FIG. 9 shows another construction similar to FIG. 8 and the same reference numerals are used to define similar parts. In this arrangement however the wings 35 are provided at the corners of the central sleeve 30. The construction of the wings 35 can be similar to those shown in FIG. 8.

Figure 10:
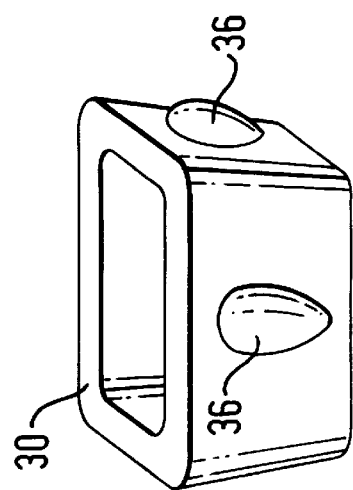
FIG. 10 is an isometric view of an alternative sleeve construction.

FIG. 10 shows another alternative construction in which a central sleeve 30 is provided with projections 36 which are shaped and dimensioned to engage the inner wall of the bone cavity 4. These projections 36 can be of any convenient shape but in FIG. 10 they are shown as being of a teardrop shape with the broad end facing towards the proximal end of the stem. As mentioned above any convenient shape can be employed and projections of a teardrop shape could also be applied in the reverse position, that is with the narrow end being towards the proximal end of the stem. The material could also be deformable or resilient to provide a grip on the inner wall of the bone cavity.

Figure 11:
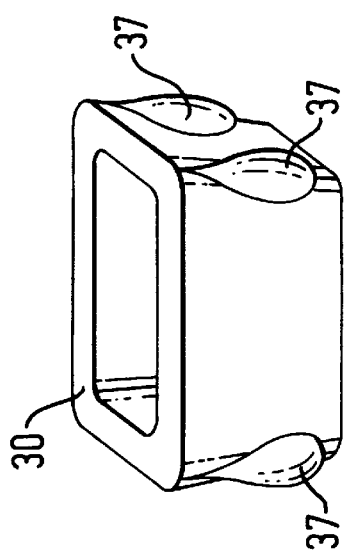
FIG. 11 is an isometric view of yet another alternative construction.

FIG. 11 shows another alternative construction in which projections 37 are employed but in this arrangement they are provided on the corners of the sleeve 30 and, as will be seen, are of teardrop shape with the narrow end extending towards the proximal end of the stem.

Figure 12:
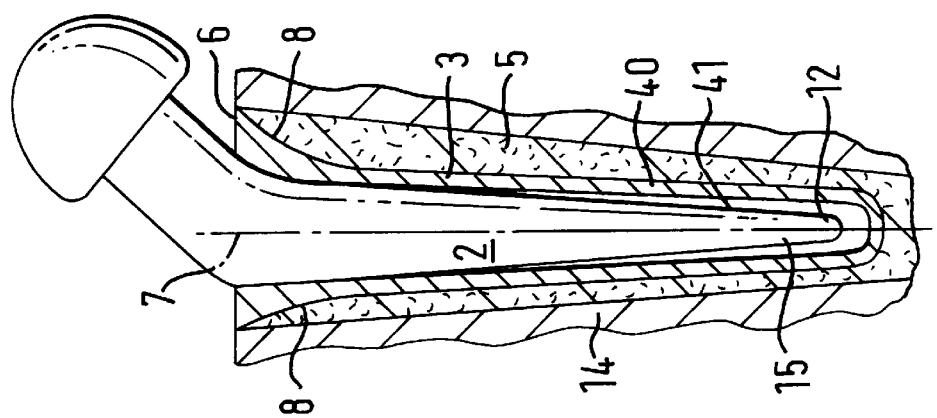
FIG. 12 is a cross-sectional side elevation of another construction according to the invention.

FIG. 12 shows another construction similar to that shown in FIG. 5 and the same reference numerals are used to indicate similar parts. In this construction however the mantle is shaped and dimensioned to only engage the proximal part of the stem down to about half way or less. The distal portion 40 of the mantle can be parallel sided or tapered so that it creates a void 41 which extends up to half of the length of the mantle from the distal end. This acts to limit the length of engagement of the stem with the mantle, the intention being to limit the load transfer between the stem and the bone so that it takes place in the proximal portion of the bone opening.

This concept can also be applied to the construction shown in FIGS. 1, 2, 3 or 4. It will again be appreciated that the mantle can be preformed as a separate article and suitably dimensioned and adapted for subsequent fitting to the stem of the prosthesis.

In all the constructions described above the outer edges or surfaces of the sleeve are shown in contact with the wall of the bone cavity 4. In certain circumstances this may be undesirable and the sleeve can therefore be dimensioned so that there is a gap around the contact surfaces which will be filled with cement. The gap will be small enough to ensure that the guiding effect of the sleeve is achieved but intimate contact of the sleeve material with the inner wall of the bone cavity is avoided. Thus, there will always be some cement dough which then polymerises between the preformed mantle and the endosteal surface of the femur. This will ensure that the cement can take a "mirror image" cast of the inside of the relevant part of the canal and such a cast may be important for the subsequent formation of living bone in contact with the cement. The overall effect however is similar to that which is achieved if the sleeve makes actual contact with the inner wall.

What is claimed is:

1. A prosthesis for implantation into an open end of a bone cavity with bone cement comprising:
   a stem to be inserted into the bone cavity having a first end adjacent the open end of the cavity and a second end opposite said first end;
   a sleeve made of bone cement material for insertion into the bone cavity, said sleeve having a solid wall defined by an outer surface and an internal opening in said sleeve for receiving said stem, said wall increasing in thickness adjacent the open end of the bone cavity forming an outwardly projecting balcony, an outermost projection of said balcony adjacent the open end of the bone cavity, at least part of said outer surface of said sleeve spaced from internal walls of said cavity.

2. The prosthesis as claimed in claim 1 in which said sleeve extends over only a part of the length of the stem adjacent the open end of the bone cavity.

3. The prosthesis as claimed in claim 1 in which said sleeve extends over the whole length of the stem.

4. The prosthesis as claimed in claimed 1 in which the sleeve wall thickness which is increased towards the open bone cavity end provides an outwardly projecting balcony.

5. The prosthesis as claimed in claim 4 in which the sleeve is formed with one or more concave surfaces, the adjacent the first stem end or ends of which form said balcony.

6. The prosthesis as claimed in claim 5 in which the sleeve outer surface has a cross-section which is generally circular in shape which outer surface is conical or frusto-conical on moving along the sleeve towards said balcony.

7. The prosthesis as claimed in claim 4 in which the outer shape of the sleeve is formed with one or more substantially flat surfaces a proximal end or ends of which form said balcony.

8. The prosthesis as claimed in claim 4 in which the sleeve has an outer shape which includes three or more flat surfaces which are curved inwardly from its proximal end.

9. The prosthesis as claimed in claim 7 in which the sleeve has a cross-sectional outer shape which is triangular, square or rectangular.

10. The prosthesis as claimed in claim 1 in which said sleeve extends over the whole length of the stem, the end of the sleeve enclosing the stem and the sleeve being provided with a cup into which the second end of the stem can subsequently sink.

11. The prosthesis as claimed in claim 1 in which said internal opening of said sleeve is spaced from said stem from said second end thereof to at least about halfway to the first end thereof to limit the length of engagement between the stem and the sleeve so that loading of the bone occurs nearer the open end of the bone cavity.

12. The prosthesis as claimed in claim 1 in which the sleeve is provided with projections for centralizing the stem in the bone into which it is to be fitted.

13. The prosthesis as claimed in claim 1 in which the sleeve covers the stem from a point adjacent the open end of the bone when the stem is inserted to a point spaced away from the second end of the stem.

14. The prosthesis as claimed in claim 1 in which the sleeve is preformed and subsequently fitted to the stem.

15. The prosthesis as claimed in claim 1 in which the sleeve is made from a synthetic material.

16. The prosthesis as claimed in claim 15 in which the sleeve is made from polymethylmethacrylate (PMMA).

17. The prosthesis as claimed in claim 1 in which the sleeve outer surface has outwardly extending projections formed thereon to space said sleeve from walls of the cavity.

18. A device for guiding a stem of a prosthesis into a bone cavity having an open end which stem is to be attached therein by cement, comprising a sleeve made of cement material having a solid wall having a thickness defined by an outer surface and an internal opening to receive said stem and adapted to locate on said stem at a position at or towards a first end thereof adjacent said open end of the bone, and which is dimensioned to engage a wall of the bone cavity at or towards the open end thereof to guide the first end of the stem in place therein, said sleeve outer surface having circumferentially spaced projections thereon extending in a proximal-distal direction for contacting the wall of the bone cavity and space the outer surface from the wall of the bone cavity.

19. The device as claimed in claim 18 in which said sleeve is adapted to extend over only a part of the length of the stem adjacent the first end thereof.

20. The device as claimed in claim 18 in which said sleeve is adapted to extend over the whole length of the stem.

21. The device as claimed in claim 18 in which the sleeve has a wall thickness which is increased towards its the open bone end to provide an outwardly projecting balcony.

22. The device as claimed in claim 21 in which the sleeve outer surface has a cross-section which is generally circular in shape which outer surface is conical or frusto-conical on moving along the sleeve towards said balcony.

23. The device as claimed in claim 21 in which the outer shape of the sleeve is formed with one or more substantially flat surfaces a proximal end or ends of which form said balcony.

24. The device as claimed in claim 21 in which the sleeve has an outer shape which includes three or more flat surfaces which are curved inwardly from its proximal end.

25. The device as claimed in claim 23 in which the sleeve has a cross-sectional outer shape which is triangular, square or rectangular.

26. The device as claimed in claim 18 in which said sleeve is adapted to extend over the whole length of the stem, an end of the sleeve adjacent a second end of the stem opposite the first end enclosing the stem and the sleeve being provided with a cup into which the second end of said stem can subsequently sink.

27. The device as claimed in claim 26 in which said internal opening of said sleeve is spaced from said stem from said second end thereof to at least about halfway to the first end thereof to limit the length of engagement between the stem and the sleeve so that loading of the bone occurs nearer the open end.

28. The device as claimed in claim 18 in which the sleeve is provided with projections for centralizing the stem in the bone into which it is to be fitted.

29. The device as claimed in claim 18 in which the sleeve is adapted to cover the stem from a point adjacent to the open end of the bone when the stem is inserted to a point spaced away from the second end of stem.

30. The device as claimed in claim 18 in which the sleeve is preformed and adapted to be subsequently fitted to the stem.

31. The device as claimed 18 in claim which the sleeve is made from a synthetic material.

32. The device as claimed in claim 31 in which the sleeve is made from polymethacrylate (PMMA).

33. The device as claimed in claim 21 in which the sleeve is formed with one or more concave surfaces, the end or ends of which adjacent the first end form said balcony.

\* \* \* \* \*

UNITED STATES PATENT AND TRADEMARK OFFICE
CERTIFICATE OF CORRECTION

PATENT NO.  : 6,214,053 B1
DATED       : April 10, 2001
INVENTOR(S) : Ling et al.

It is certified that error appears in the above-identified patent and that said Letters Patent is hereby corrected as shown below:

Column 2,
Line 14, "anid" should read -- and --.

Column 5,
Line 41, after "the" insert -- end --.
Line 41, cancel "adjacent".
Line 42, cancel "the first stem end".
Line 42, after "which" insert -- the end or ends of which adjacent the first stem end form said balcony "--.

Column 6,
Line 39, cancel "its".

Signed and Sealed this

Twenty-seventh Day of November, 2001

Attest:

*Nicholas P. Godici*

NICHOLAS P. GODICI
Attesting Officer    Acting Director of the United States Patent and Trademark Office